United States Patent
Gilloteaux et al.

(10) Patent No.: US 7,091,241 B2
(45) Date of Patent: Aug. 15, 2006

(54) NONTOXIC POTENTIATION/SENSITIZATION OF CANCER THERAPY BY SUPPLEMENTARY TREATMENT WITH COMBINED VITAMINS C AND $K_3$

(75) Inventors: Jacques Gilloteaux, Kent, OH (US); Henryk S. Taper, Wilsele (BE); James M Jamison, Rootstown, OH (US); Jack L. Summers, Tallmadge, OH (US)

(73) Assignee: Summa Health System, Akron, OH (US)

( * ) Notice: Subject to any disclaimer, the term of this patent is extended or adjusted under 35 U.S.C. 154(b) by 317 days.

(21) Appl. No.: 10/160,152

(22) Filed: Jun. 3, 2002

(65) Prior Publication Data

US 2003/0073738 A1  Apr. 17, 2003

Related U.S. Application Data (60) Provisional application No. 60/295,025, filed on Jun. 1, 2001.

(51) Int. Cl.
*A01N 43/08* (2006.01)

(52) U.S. Cl. .................. 514/474; 514/681; 514/684

(58) Field of Classification Search ................ 514/474, 514/681
See application file for complete search history.

(56) References Cited

U.S. PATENT DOCUMENTS 6,087,350 A  7/2000  Johnson et al.

OTHER PUBLICATIONS

PubMed, Taylor et al, Can J Biochem Physiol Sep. 1957, 35 (9) 691-7, abstract.*

CMAJ-JAMC on line, Padayatty et al, CMAJ, Feb. 6, 2001, 164 (3), p. 1-6.*

Noto, Vencenzo; Taper, Henryk S.; Yi-Hua, Jiang; Janssens, Jaak; Bonte, Jan; De Loecker, William; *Effects of Sodium Ascorbate(Vitamin C) and 2-Methyl-1,4- Napthoquinone (Vitamin $K_3$) Treatment of Human Tumor Growth in Vitro, I. Synergism of Combined Vitamin C and $K_3$ Action*; Cancer, Mar. 1, 1989, vol. 63.

Taper, H and Roberfroid, M.; *Cancer Chemotherapy Potentiation Induced by Combined Vitamin C and Vitamin $K_3$ with Ferrous Sulfate Pretreatment*; Oncology (Life Science Adv.) 1992 11:19-25.

Taper, Henryk S.; de Gerlache, Jacques; Lans, Marc, Roberfroid, Marcel; *Non-Toxic Potentiation of Cancer Chemotherapy by Combined C and $K_3$ Vitamin Pretreatment*; Int. J. Cancer; 1987, 40; 575-579.

(Continued)

*Primary Examiner*—Ardin H. Marschel
*Assistant Examiner*—James D. Anderson
(74) *Attorney, Agent, or Firm*—Brouse McDowell; Roger D. Emerson; Daniel A. Thomson (57) ABSTRACT

A combination of Vitamin C and a quinone used as a supplemental treatment for a cancer patient. The combination may be administered before, during and after the patient undergoes a conventional cancer treatment protocol. The combination may be administered orally, intravenously, or intraperitoneally. Oral administration may be in the form of capsules containing a predetermined ratio of Vitamin C to Vitamin $K_3$. The supplemental treatment is effective to inhibit metastases of cancer cells and inhibit tumor growth. The ratio of Vitamin C to Vitamin $K_3$ is in the range of about 50 to 1 to about 250 to 1. A method for evaluating the effectiveness of the supplemental treatment includes monitoring the patient's serum DNase activity throughout the course of treatment.

23 Claims, 5 Drawing Sheets

OTHER PUBLICATIONS

Taper, H.S.; Roberfroid, M.; *Non-Toxic Sensitization of Cancer Chemotherapy by Combined Vitamin C and $K_3$ Pretreatment in a Mouse Tumor Resistant to Oncovin*; Anticancer Research 1992, 12: 1651-1654.

Taper, H. S. *Reversibility of Acid and Alkaline Deoxyribonuclease Deficiency in Malignant Tumor Cells*; The Journal of Histochemistry and Cytochemistry 1981; vol. 29, No. 9, pp. 1053-1060.

De Loecker, William, Janssen, Jaak, Bonte, Jan, and Taper, Henyrk S.; *Effects of Sodium Ascorbate(Vitamin C) and 2-Methyl-1,4-Napthoquinone (Vitamin $K_3$) Treatment of Human Tumor Growth in Vitro; II Synergism with Combined Chemotherapy Action*; Anticancer Research 13: 1993; 103-106.

Taper, Henryk S.; Keyeus, Andre, Roberfroid, Marcel; *Potentiation of Radiotherapy by Nontoxic Pretreatment of Combined Vitamin C and Vitamin $K_3$ in Mice Bearing Solid Transplantable Tumor*; Anticancer Research 16, 1996, 499-504.

* cited by examiner

NONTOXIC POTENTIATION/SENSITIZATION OF CANCER THERAPY BY SUPPLEMENTARY TREATMENT WITH COMBINED VITAMINS C AND $K_3$

This application claims priority to U.S. Ser. No. 60/295,025, entitled NONTOXIC POTENTIATION/SENSITIZATION OF CANCER THERAPY BY SUPPLEMENTARY TREATMENT WITH COMBINED VITAMINS C AND $K_3$, filed Jun. 1, 2001.

BACKGROUND OF THE INVENTION

1. Field of Invention

This invention pertains to the art of methods for the prevention and treatment of human cancer, and more specifically to methods utilizing a combination of Vitamin C and Vitamin $K_3$ for the prevention and treatment of human cancer.

2. Description of the Related Art

Metastases are one of the greatest problems in cancer patients. They appear in almost all cases of this disease and are the primary cause of mortality in cancer patients. The metastatic process begins when cancer cells escape from the primary tumor, invade the basement membrane of regions capillary vessels and traverse into the blood or lymph and migrate to distant organs or tissues. There they form vascular emboli from which the cancer cells cross the basement membrane of capillary vessels for the second time and colonize the new tissue or organ. Different mechanisms are involved in the so-called metastatic cascade, including angiogenesis, cellular adhesion, local proteolysis and tumor cell migration. Development of chemotherapeutic agents that target and intervene in one or more processes in the metastatic cascade should lead to a favorable outcome for a large number of cancer patients.

In the art there has been much attention focused on the role of vitamins in cancer prevention and treatment. For example, it is known that Sodium Ascorbate, hereafter referred to as Vitamin C, has been shown to provide improved effects to certain cancer treatments. Vitamin C potentiates the growth inhibitory effect of certain agents and increases the cytotoxicity of other agents. It is considered that Vitamin C may even reverse malignant cell transformation.

Similarly, it has been reported in the art that 2-Methyl-1,4-Naphthoquinone, hereafter referred to as Vitamin $K_3$, provides improvements in the field of cancer treatment.

Research has been conducted on the combination of Vitamin C and Vitamin $K_3$ to determine the usefulness of the combination as a cancer chemotherapy potentiating agent.

One publication, entitled EFFECTS OF SODIUM ASCORBATE (VITAMIN C) AND 2-METHYL-1,4-NAPHTHOQUINONE (VITAMIN $K_3$) TREATMENT ON PATIENT TUMOR CELL GROWTH IN VITRO (1989), teaches that Vitamin C tends to accumulate in tumors, may reverse malignant cell transformation, may demonstrate cytotoxic action toward tumor cells, and requires high dosages to achieve an inhibiting effect when administered alone. The article teaches that Vitamin $K_3$ inhibits growth of mammalian tumor cells in a culture, and requires high dosages to achieve a desirous effect when administered alone.

A second publication, entitled NON-TOXIC POTENTIATION OF CANCER CHEMOTHERAPY BY COMBINED C AND $K_3$ VITAMIN PRE-TREATMENT (1987) discloses in vivo (mice) intraperitoneal injection of Vitamin C at 1 g/Kg and $K_3$ at 10 mg/Kg before or after a single treatment of several cytotoxic drugs.

POTENTIATION OF RADIO THERAPY BY NON-TOXIC PRETREATMENT WITH COMBINED VITAMINS C AND $K_3$ IN MICE BEARING SOLID TRANSPLANTABLE TUMOR (1996) discusses the use of a Vitamin C/Vitamin $K_3$ combination in conjunction with radiotherapy cancer treatments.

CANCER CHEMOTHERAPY POTENTIATION INDUCED BY COMBINED VITAMIN C AND $K_3$ WITH FERROUS SULFATE PRETREATMENT (1992) teaches administration of Vitamin C and Vitamin $K_3$ prior to treatment with certain chemotherapeutic agents.

NON-TOXIC SENSITIZATION OF CANCER CHEMOTHERAPY BY COMBINED VITAMIN C AND $K_3$ PRETREATMENT IN A MOUSE TUMOR RESISTANT TO ONCOVIN (1992) discusses the use of an intraperitoneal injection of Vitamin C and Vitamin $K_3$ as a pretreatment in order to increase tumor sensitization to the action of Oncovin.

EFFECTS OF SODIUM ASCORBATE (VITAMIN C) AND 2-METHYL-1, 4-NAPHTHOQUINONE (VITAMIN $K_3$) TREATMENT ON PATIENT TUMOR CELL GROWTH IN VITRO. II. SYNERGISM WITH COMBINED CHEMOTHERAPY ACTION (1993) reports the results of additional in vitro studies involving simultaneous exposure to Vitamin C and Vitamin $K_3$.

Each of the publications identified above is incorporated in its entirety by reference into this specification.

There remains a need in the art for improved methods of enhancing the efficacy of cancer treatments. The present invention is directed to a method of treating a patient having cancer by supplemental treatment with a combination of VC/VK$_3$. The supplemental treatment is utilized prior, during, and following the use of conventional cancer treatments, such as radiology and chemotherapy. Specifically, the present invention is directed toward a clinical dosing protocol. Still further, the present invention is directed to methods of preparation of both oral and intravenous delivery systems of the VC/VK$_3$ combination.

The present invention is further directed to methods of determining the effectiveness of the supplemental treatments. The improved methods further provide indications of when additional supplemental treatments should be administered.

SUMMARY OF THE INVENTION

In accordance with the present invention, there is provided a clinical protocol for the administration of a supplemental cancer treatment utilizing a combination of VC/VK$_3$.

In accordance with the invention, there is provided a method of inhibiting metastasis of cancer cells sensitive to the effects of a vitamin C/quinone combination which comprises administering to a host in need of such inhibiting, a combination of Vitamin C and a quinone wherein the combination is administered in an amount synergistically effective to inhibit metastasis of cancer cells.

In accordance with the invention, the administering step includes following a predetermined dosing regimen for administering the combination.

In accordance with the invention the predetermined dosing regimen includes providing a first phase of treatment with the combination; and, providing a subsequent phase of treatment following the first phase.

In accordance with the invention, the combination is administered as a supplemental treatment in conjunction with a conventional cancer treatment protocol.

In accordance with the invention, the quinone is Vitamin $K_3$.

In accordance with the invention, there is provided a dosing regimen for a combination of Vitamin C and a quinone for use in treating a host in conjunction with a conventional cancer treatment protocol, the dosing regimen comprising: a first phase wherein a first amount of the combination is administered to the host each day from an initial treatment day up until two days prior to subjecting the host to a conventional treatment according to a conventional cancer treatment protocol; a second phase wherein a second amount of the combination is administered to the host for each of two days prior to subjecting the host to the conventional cancer treatment protocol; a third phase wherein a third amount of the combination is administered to the host on a same day as the host is subjected to the conventional cancer treatment protocol; a fourth phase wherein a fourth amount of the combination is administered to the host on the day following the conventional cancer treatment protocol.

In accordance with the invention, there is provided a method for monitoring the effectiveness of a supplemental cancer treatment, the monitoring method comprising the step of administering a supplemental cancer treatment to a patient; and, measuring a serum alkaline DNase activity of the patient before, during, and after the step of administering the supplemental cancer treatment.

In accordance with the invention, there is provided a method of inhibiting tumor growth in a tumor sensitive to the effects of a Vitamin C/quinone combination which comprises administering to a host in need of such inhibiting, a combination of Vitamin C and a quinone wherein the combination is administered in an amount synergistically effective to inhibit tumor growth.

In accordance with the invention, there is provided a cancer supplemental treatment kit comprising a plurality of capsules, each of the capsules comprising a combination of Vitamin C and a quinone.

BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein.

DESCRIPTION OF THE PREFERRED EMBODIMENT

The following definitions are given to clarify the usage of terms herein. "Neoplastic" denotes a type of cell exhibiting uncontrolled proliferation. Generally, mitotic progeny of a neoplastic cell are also neoplastic in character and do not terminally differentiate in vivo in response to physiologically normal (nonpathological) endogenous (not exogenous or invasive) environmental cues. Neoplastic cells include cancerous and transformed cells. Neoplastic cells can be isolated in the body (a metastatic or disseminated neoplastic cell) or aggregated, either homogeneously or in heterogeneous combination with other cell types in a tumor or other collection of cells. In this regard, a "tumor" includes any collection of cells (neoplastic or otherwise) in which at least some of the member cells are physically associated with at least some other member cells through a common extracellular matrix.

"Autoschizic cell death" is the term used to denote a type of necrosis characterized by exaggerated membrane damage and progressive loss of organelle-free cytoplasm through a series of self-excisions.

"Synergistic effective amount" denotes an amount of vitamin C and a quinone in accordance with the invention that is effective to produce advantageous results when the vitamin C and quinone are used in combination, rather than results obtained by vitamin C and a quinone used individually to treat a host.

Figure 1:
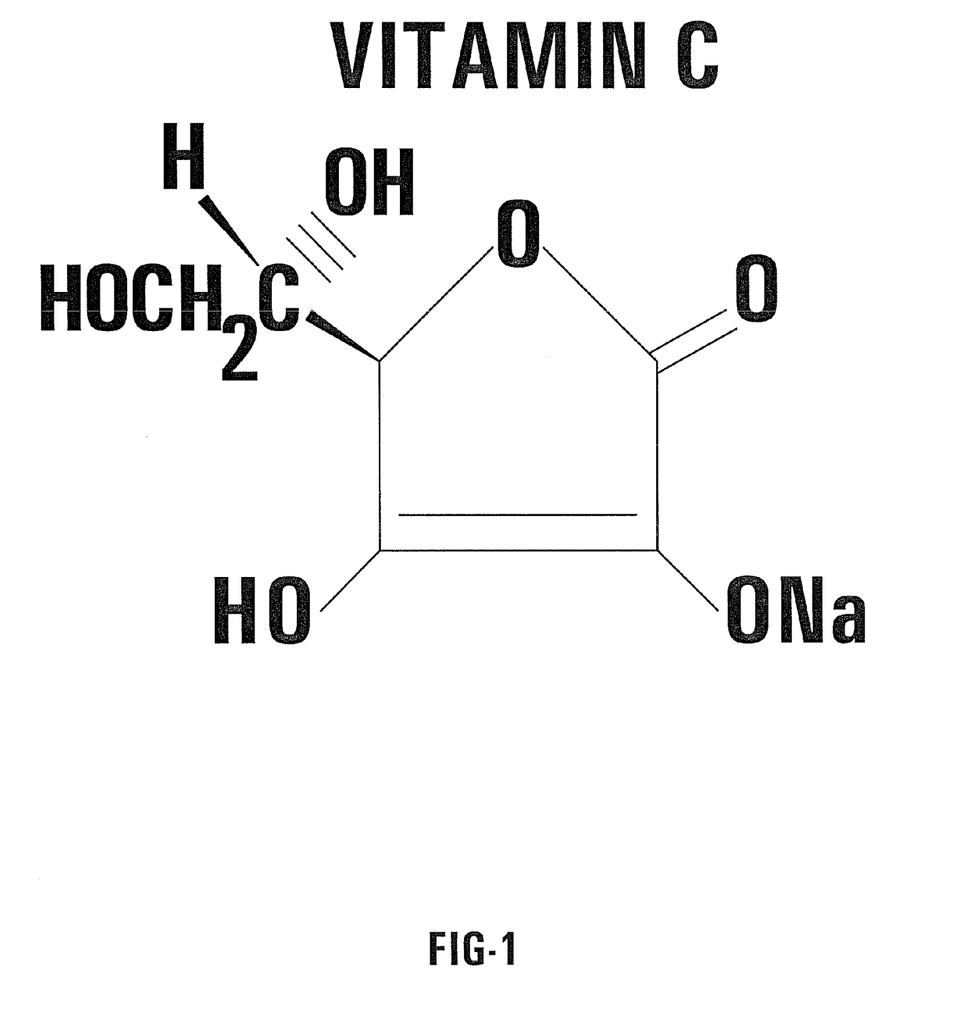
FIG. 1 illustrates the structural formula of Vitamin C.
Figure 2:
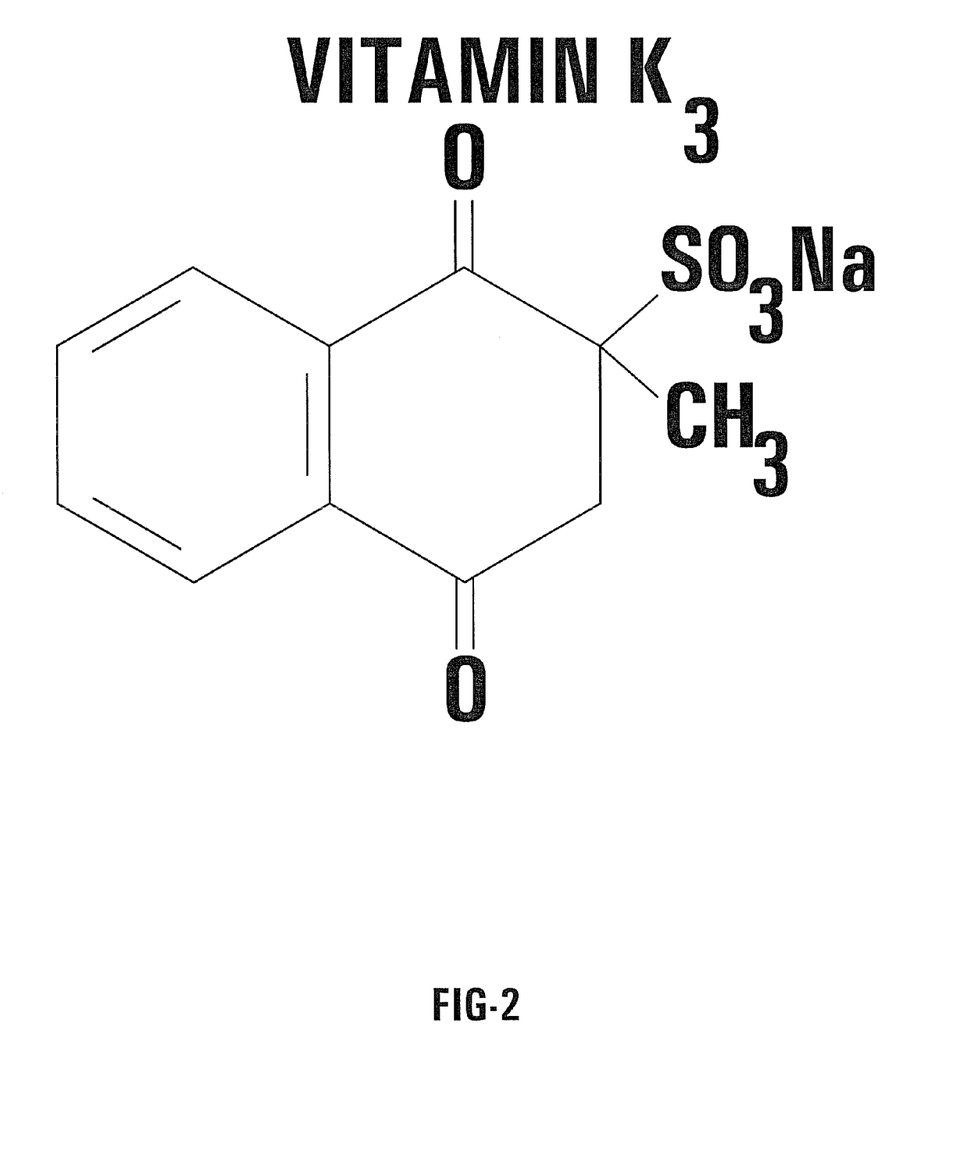
FIG. 2 illustrates the structural formula of Vitamin $K_3$.

The present invention is directed toward cancer treatment protocols that include a supplemental administration of a Vitamin C/quinone combination in conjunction with other conventional cancer treatments. Benzoquinone is an example of a quinone that has been shown to inhibit the metastasis of several colon cancer lines that had been implanted into immunocompetent mice. In accordance with the present invention, a preferred quinone is Vitamin $K_3$. The preferred form of Vitamin $K_3$ is the bisulfite form that is water soluble, and does not build up in the lipids of the subject. In this description of the preferred embodiment, reference is made to a preferred embodiment utilizing Vitamin $K_3$, however, the invention is not thereby limited. FIG. 1 illustrates the structural formula of Vitamin C (10). FIG. 2 is directed to the structural formula of the bisulfite form of Vitamin $K_3$ (12).

It has been discovered that the $VC/VK_3$ combination exerts antitumor and antimetastatic activities through a wide array of mechanisms including: blockage of the cell cycle, modulation of signal transduction and potentiation of the immune system, and induction of necrosis characterized by exaggerated membrane damage and the progressive loss of cytoplasm through a series of self-excisions. This action is termed "autoschizic cell death" in this disclosure.

As a cancer treatment protocol, in its widest scope, the present invention provides a method of killing a cell with a neoplastic disorder within a patient by supplemental treatment with a predetermined regimen of a $VC/VK_3$ combination, in conjunction with conventional cancer treatment such as radiotherapy, chemotherapy, or brachiotherapy. The supplemental treatment begins prior to an initial conventional cancer treatment, and continues into the interval between subsequent conventional treatments.

This approach is effective in treating patients having intact tumors. For example, it is known in the art that when a tumor grows to a certain size, then eventual metastases becomes predictable. Use of the present invention retards or inhibits tumor growth. Therefore, the inventive method reduces the likelihood that cells from such tumors will eventually metastasize or disseminate.

The inventive method can reduce or substantially eliminate the potential for further spread of neoplastic cells throughout the patient, thereby also reducing or minimizing the probability that such cells will proliferate to form novel tumors within the patient. In the event that the preventive method achieves substantial reduction or elimination of the tumor, then the pathogenic effects of such tumors within the patient are attenuated.

In the preferred vitamin combination of the present invention, the preferred ratio of the amount of Vitamin C to Vitamin $K_3$ is 100 to 1. This preferred ratio will be referenced in this specification as exemplary only and not by way of limiting the invention. However, in its widest scope, the present invention has been shown to be an effective cancer treatment protocol when the ratio of the amount of Vitamin C to the amount of Vitamin K ranges between 50 to 1 and 250 to 1.

In the dosing regimen, the maximum dosage of the combination is limited by the Vitamin $K_3$ dose, since Vitamin $K_3$ is believed to be toxic at high concentrations.

Where both vitamins are delivered orally, the dosage of Vitamin C may range from about 33.3 mg/Kg (body weight)/day to a maximal amount of about 1 g/Kg/day. The dosage of Vitamin $K_3$ may range from about 0.17 mg/Kg/day to a maximal amount of about 200 mg/Kg/day. In a preferred embodiment, the ratio of vitamin C to vitamin $K_3$ is about 50 to 1. In another preferred embodiment, the ratio of vitamin C to vitamin $K_3$ is about 250 to 1. In yet another preferred embodiment, the ratio of vitamin C to vitamin $K_3$ is about 100 to 1. In the preferred embodiment, the ratio of vitamin C to vitamin $K_3$ is preferably in the range of 50 to 1 to 250 to 1, respectively.

In the case where both vitamins are delivered intravenously or intraperitoneally, the dosage of Vitamin C may be is as low as 1 g/Kg/day. In a preferred embodiment, the dosage of Vitamin C may be about 100 g/Kg/day. In another preferred embodiment, the dosage of Vitamin C may be up to about 625 g/Kg/day. In another preferred embodiment, the dosage of Vitamin C may be in the range of about 1/g/Kg/day to up to about 625/g/Kg/day.

The dosage of Vitamin $K_3$ may be as low as about 20 mg/Kg/day. In a preferred embodiment, the dosage of Vitamin $K_3$ may be 1 g/Kg/day. In another preferred embodiment, the Vitamin $K_3$ may be up to about 2.5 g/Kg/day. In another preferred embodiment, the dosage of Vitamin $K_3$ may be in the range of about 20 mg/Kg/day to about 2.5 g/Kg/day.

In the practice of the present invention, the vitamin combination can be administered by any suitable manner, i.e., orally, intravenously, or intraperitoneally. The vitamins can also be delivered, for example, by injection of vitamin $K_3$, and administration of Vitamin C in drinking water. In a preferred embodiment, both oral and intravenous administration is utilized.

EXAMPLE I

Capsule Formulation

The preferred embodiment of the invention utilizes an oral delivery system for a portion of the supplemental treatment regimen. In the preferred embodiment, capsules of a combination of VC/VK$_3$ are prepared. Each capsule according to the invention contains the vitamins in a predetermined ratio. For example, 0.5 g of sodium ascorbate (L-Ascorbic acid sodium salt) is combined with 0.005 g of water soluble vitamin $K_3$ (menadione sodium bisulfite). In the preferred embodiment, both vitamins are mixed in the powdered form and placed in capsules without any supplementary ingredients. In this example, the predetermined ratio is 100 to 1.

EXAMPLE II

IV Preparation

The preferred embodiment of the invention further utilizes intravenous delivery for another portion of the supplemental treatment regimen. In the preferred embodiment, solutions of vitamin C and vitamin $K_3$ are prepared and stored separately and mixed directly before intravenous infusion. Exemplary intravenous solutions are prepared as follows:

Solution of Vitamin C: 5 g Sodium ascorbate; 1.2 g NaCl; 300 ml Sterile, apyrogenic water for injection.

Solution of Vitamin Kg: 50 mg Menadione sodium bisulfite; 5 ml Sterile, apyrogenic water for injection.

These solutions must be oxygen-free (e.g. perfused with gaseous nitrogen); sterilized by filtration (millipore filters of pore diameter approximately 0.22 nm); and introduced into sterile and devoid of oxygen pockets for the vitamin C solution or glass vials for vitamin $K_3$ solution. Each series of prepared pockets or vials must be examined for apyrogenicity and sterility by methods known in the art. Since both vitamins are oxygen, light, and temperature sensitive, the solutions should be stored in anoxic conditions at approximately 4° C. in darkness to insure their effectiveness.

Alternately, the intravenous solution may be prepared by mixing 5 grams of Vitamin C and 50 mg of Vitamin $K_3$ in 300 ml of sterile non-pyrogenic normal saline in an IV bag immediately prior to use.

EXAMPLE III

Treatment Regimen

In the preferred embodiment, the treatment regimen is divided into distinct phases. Phase I includes the period of time prior to treatment with conventional cancer treatment (e.g. radiotherapy, chemotherapy, brachiotherapy), ending with two days prior to conventional treatment. Phase I is designated $-t_x$. Phase II comprises the day before the convention treatment and is designated $-t_1$. Phase III comprises the day of the conventional cancer treatment and is designated $t_0$. Phase IV comprises the day following the conventional cancer treatment and is designated $+t_1$. Phase V is the period of time following Phase IV and is designated $+t_x$. If additional conventional treatments are to be used on the patient, then the cycle repeats so that Phase V melds into Phase I of the next cycle.

In the preferred embodiment, Phase I includes at least two weeks and more preferably includes four weeks. Additionally, Phase V preferably includes the entire period of time prior to a next conventional treatment, if any, which are generally spaced from four to six weeks apart.

The preferred supplemental treatment regimen is as follows:

| | |
|---|---|
| Phase I: | 4 capsules per day taken at 5-hour intervals; |
| Phase II: | 10 capsules per day taken at 2-hour intervals; |
| Phase III: | 10 capsules per day taken at 2 hour intervals, plus intravenous delivery of up to 5 g Vitamin C and 50 mg Vitamin $K_3$, prepared as above, at least approximately 30 minutes, but less than approximately 3 hours prior to the conventional treatment; |
| Phase IV: | 10 capsules per day taken at 2-hour intervals; |
| Phase V: | 4 capsules per day taken at 5-hour intervals. |

The preceding dosing regimen is provided for exemplary purposes only and not by way of limiting the invention.

EXAMPLE IV

Case Study I

The following example demonstrates the efficacy of the present invention. In particular the example demonstrates that pretreatment of neoplastic cells with a VC/VK$_3$ combination increases the efficiency of conventional cancer treatments. This example is included here merely for illustrative purposes and should not be construed so as to limit any aspect of the claimed invention.

This case study concerns a woman with recurrent breast cancer with pea-size metastases to the vertebral column. After the primary tumor had been surgically removed, she was subjected to four cycles of traditional chemotherapy. However, new metastases were observed and existing metastases were seen to grow following each of the four cycles of chemotherapy. Immediately following the last of these four chemotherapy sessions, the patient took 2 g of Vitamin C and 20 mg of Vitamin K$_3$ (4 capsules total) orally at approximately five-hour intervals. On the day preceding, the day of, and the day following chemotherapy, the patient received 5 g of Vitamin C and 50 mg of Vitamin K$_3$ (10 capsules total) orally at approximately two-hour intervals. In addition to the oral dosage, approximately thirty minutes prior to another chemotherapy treatment, the patient received an intravenous solution of 4.5 g Vitamin C and 45 mg of Vitamin K$_3$. On the second day following chemotherapy, she resumed taking 2 g of Vitamin C and 20 mg of Vitamin K$_3$ (4 capsules total) orally at approximately five-hour intervals until the day prior to the next chemotherapy. Following one cycle of this regimen, no new metastases were observed and existing metastases were observed to decrease in size. The metastases continued to be diminished with each subsequent cycle of chemotherapy. After 5 cycles of chemotherapy, the patient's cancer went into remission and she has been cancer free for over four years.

EXAMPLE V

Case Study II

This case study involves a man with colon cancer who had large and abundant metastases to the liver. This end-stage cancer patient had been undergoing chemotherapy with 5-fluorouracil and other chemotherapeutic agents and was suffering many side effects from the treatment. In addition, he was bloated with ascites fluid and was expected to die within 2 months. The patient received oral dosages of a vitamin C (2.0 g/day)/vitamin K$_3$ (0,020 g/day) combination in conjunction with the chemotherapy. While the vitamin combination was not curative, it did substantially ameliorate the side effects of the chemotherapy. In addition, he survived relatively pain free and was lucid until his death nearly two years later.

EXAMPLE VI

Evaluation of Vitamin-Induced Changes in Life Span of Nude Mice

Figure 3:
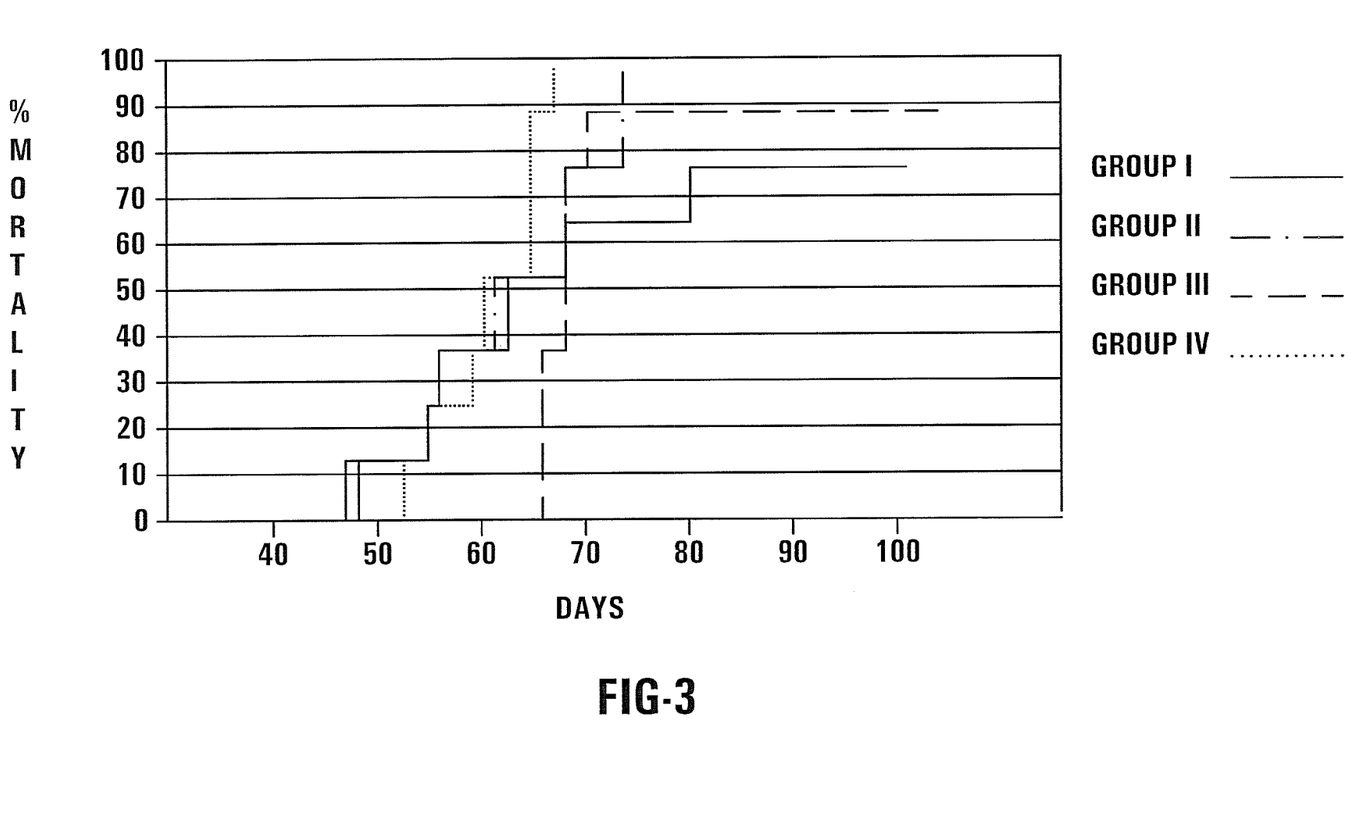
FIG. 3 is a graph showing the results of a study involving four groups of male athumic nude mice.

Male athymic nude mice (NCCr-nu/nu; 4 weeks old) were purchased from Taconic Farms (Germantown, N.Y.) and maintained in microinsulator cages (within the AALAC accredited NEOUCOM Comparative Medicine Unit) in a pathogen-free isolation facility. After a one-week isolation period, the nude mice were divided into four groups of eight animals. Group I received the vitamin combination daily for one week by oral gavage prior to tumor injection. Group II received a single intraperitoneal injection of the vitamin combination 48 hours after tumor inoculation. Group III received both oral and intraperitoneal vitamin combination at the dosages and regimen described for Groups I & II. Group IV received a single intraperitoneal injection of the administration vector. All mice were inoculated with $5.0 \times 10^6$ DU145 cells and the date of death was recorded. Mice surviving 90 days post tumor inoculation were considered long term survivors. FIG. 3 illustrates the % mortality vs. days for this study.

The mean survival days and percentages of long term survivors are summarized in TABLE I below:

TABLE I

| Group Number | Mean Survival Days | Long Term Survivors |
|---|---|---|
| I | 71 ± 15 | 25% |
| II | 66 ± 12 | 0% |
| III | 69 ± 4.6 | 12% |
| IV | 60 ± 4.7 | 0% |

One month after the death of the last control mouse, surviving mice were sacrificed and autopsied. These mice showed little if any tumor burden (4–6 tumors vs. 40–60 tumors for control mice.) The similarity in mean survival days for Groups I & III suggest that the oral vitamin administration may be the most effective route of delivery.

With reference to TABLE 1, the mortality rates of the test groups are shown. In Group III, the first mouse died on day 45, however, an autopsy revealed a low amount of tumor burden. Liver necrosis and signs of infection suggested that the mouse died from infection, not tumor load. Therefore, the first tumor-related death of mice in Group III occurred four days after the death of the last control mouse.

EXAMPLE VII

Measurement of Vitamin-Induced Changes in Solid Tumor Volume

Four week old male athymic nude mice were held in isolation for one week. Subsequently, $1 \times 10^6$ DU145 cells suspended in 0.1 ml of matrigel were injected subcutaneously into the interscapular region. After tumors of sufficient size had developed (a minimum of 3 mm in the smallest dimension), the mice were weighed, randomized, and divided into four groups of eight animals. Group A received the vitamins ad libitum in their drinking water for the duration of the study. Group B received the vitamins twice per week by subcutaneous injection near the tumor. Group C received vitamins in their drinking water and by subcutaneous injection at the doses and regimen described in Groups A and B. Group D received only water. The weight and tumor size of individual mice were determined weekly. Tumor volume was calculated using the formula: V $(L \times W^2)/2$, where V=volume, L=length, and W=width. After 3 weeks of vitamin exposure, the mice were sacrificed and major organs were removed, weighed and histologically examined.

The change in the volume of the tumors is given for each group in Table II below:

TABLE II

| GROUP | TIME IN WEEKS | | | |
|---|---|---|---|---|
| | 0 | 1 | 2 | 3 |
| A | 0.098 ± 0.047 | 0.313 ± 0.147 | 0.657 ± 0.222 | 0.918 ± 0.308 |
| B | 0.086 ± 0.032 | 0.511 ± 0.293 | 1.186 ± 0.579 | 1.207 ± 0.308 |
| C | 0.077 ± 0.032 | 0.320 ± 0.122 | 0.541 ± 0.228 | 0.963 ± 0.400 |
| D | 0.073 ± 0.035 | 0.498 ± 0.169 | 0.959 ± 0.346 | 1.420 ± 0.492 |

Volume given in cm$^3$

In this example, oral vitamin administration resulted in statistically significant slowing of tumor growth, while subcutaneous vitamin administration had no effect on the rate of tumor growth. The fact that the oral vitamins were administered ad libitum in the drinking water suggests that the continuous presence (of even small doses) or periodic introduction of small doses of the vitamins may be more effective in controlling the growth of the tumor than gavage of a larger dose of the vitamins.

The results of the histological examination of major organs for Group A and Group D (control) is given in Table III below:

TABLE III

| GROUP | Heart | Kidney | Liver | Lungs | Spleen |
|---|---|---|---|---|---|
| A | 0.166 ± 0.020 | 0.616 ± 0.057 | 2.294 ± 0.263 | 0.206 ± 0.008 | 0.227 ± 0.027 |
| D | 0.198 ± 0.010 | 0.703 ± 0.069 | 2.883 ± 0.245 | 0.235 ± 0.026 | 0.245 ± 0.088 |

None of the organs of the vitamin treated mice exhibited a weight that was significantly different from the control mice. Histological examination for signs of vitamin-induced pathology to the heart, kidneys, liver, lungs, spleen, the epithelial lining of the intestinal tract, and bone marrow revealed that vitamin treatment at these doses did not produce any apparent non-specific toxicity to the host mice.

EXAMPLE VIII

Influence of Orally Administered VC/VK$_3$ on the Metastasis of Mouse Liver Tumor (T.L.T) Cells Implanted in C3H Mice Young adult male C3h mice were given water, containing VC/VK$_3$ (15 g//0.15 g dissolved in 1000 ml) beginning two weeks before tumor transplantation until the end of the experiment. Control mice received water ad libitum. T.L.T. cells (10$^6$) were implanted intramuscularly in the right thigh of the mice. All mice were sacrificed 42 days after tumor transplantation. Primary tumor, lungs, lymph nodes and other organs or tissues suspected of harboring metastases were examined macroscopically. Samples of primary tumors, their local lymph nodes, lungs and main organs such as liver, kidneys, spleen were taken for detailed histological examination.

42% of control mice exhibited lung metastases and 27% possessed metastases in local lymph nodes metastases whereas 24% of vitamin-treated mice exhibited lung metastases and 10% possessed local lymph nodes metastases. Furthermore, the total number of lung metastases was 19 in control group and 10 in vitamin C and K$_3$-treated mice. Histopathological examination of the metastic tumors from the vitamin-treated mice revealed the presence of many tumor cells undergoing autoschizic cell death.

Oral vitamin C and K$_3$ significantly inhibited the development of metastases of T.L.T. tumors in C3H mice. It is believed that at least a portion of this inhibition was due to the ability of the vitamin combination to induce autoschizic cell death.

EXAMPLE IX

Patient Monitoring

The effectiveness of the supplemental treatment according to the invention can be monitored for any given patient utilizing a method for cancer therapy prognosis based on the variations of serum alkaline DNase activity ("SADA").

The concept of serum alkaline DNase activity (SADA) measuring as a means for cancer therapy prediction and post-therapeutic monitoring of cancer patients is based on histochemical observations that the DNase was deficient in normecrotic cancer cells and was reactivated in early states of cancer cells necrosis both that of spontaneous origin as that induced by efficient treatment.

Figure 4:
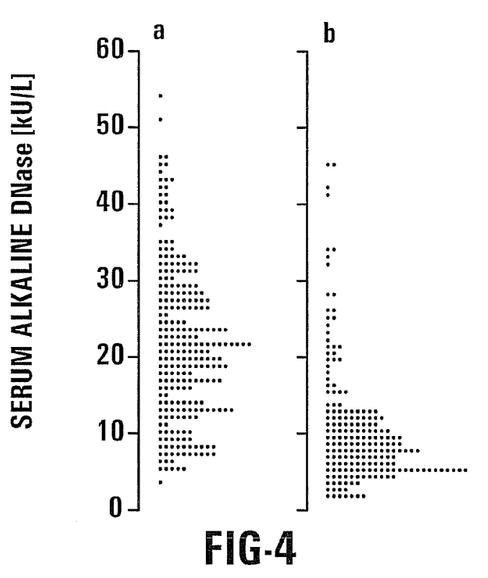
FIG. 4 illustrates serum alkaline deoxyribonuclease activity in healthy individuals and in cancer patients.

Due to the great inter-individual differences of SADA levels between the cancer bearing patients before treatment, as well as due to the lack of distinct differences of SADA levels between cancer bearing patents and normal individuals the test based on SADA measuring cannot be utilized as a diagnostic means for cancer detection. For example, FIG. 4 illustrates the serum alkaline deoxyribonuclease activity in (a) healthy individuals and in (b) cancer patients. However, multiple measuring of SADA in cancer patients during and after the treatment is certainly useful and valuable means for therapeutic prognosis and post-therapeutic monitoring of cancer patients.

Figure 5:
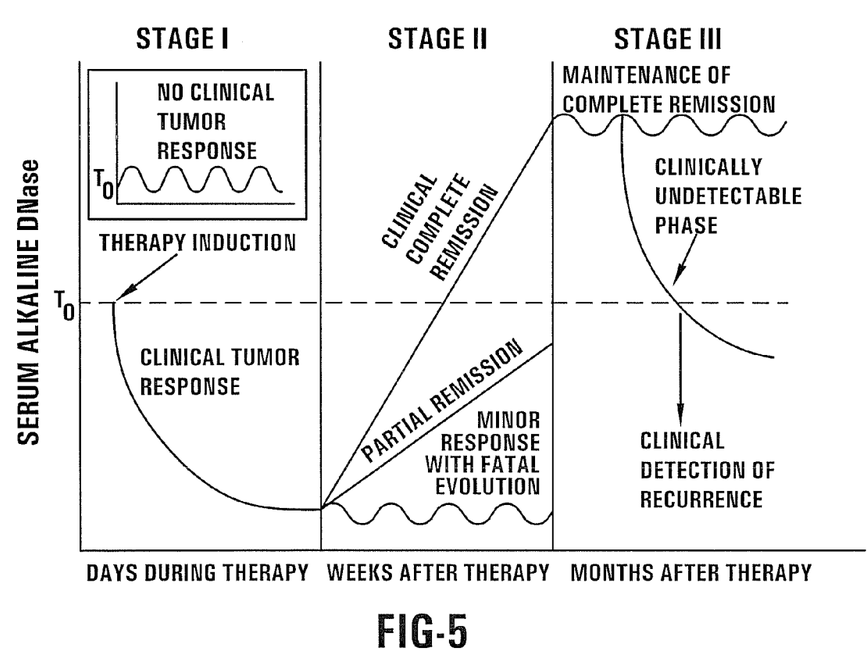
FIG. 5 is a schematic representation of serum alkaline DNase activity verses clinical response in patients with a malignant tumor.

The curves of this sensitive prognostic marker have 3 stages as illustrated in FIG. 5: Stage I (days after treatment) presents a decrease of SADA in good responders to the treatment and unchanged levels in non-responders. Stage II (weeks after treatment) demonstrates an increase of SADA higher than the initial value before treatment in complete remissions, lower increase in partial remissions and no SADA increase in tumor progression. Stage III (months after treatment) is characterized by the maintenance of post-therapeutic higher level in cases with the maintenance of remission and by the successive decrease of SADA values without any simultaneous treatment which precedes several weeks the clinical detection of recurrence. T$_o$ indicates the serum alkaline deoxyribonuclease activity level of the patient at the time of initial diagnosis, before therapy.

Figure 6:
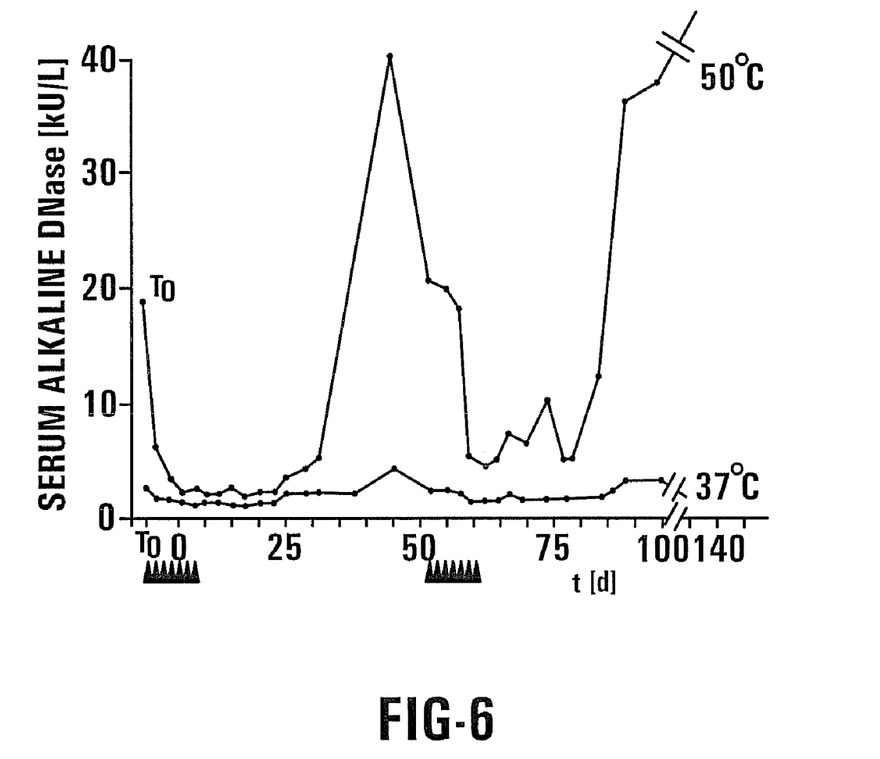
FIG. 6 illustrates the variation of serum alkaline DNase activity in a cancer patient over time.

Above described SADA variations were investigated and compared to the clinical evolution of cancer in more than 600 patients with lymphomas; bronchogenic carcinomas, nonlymphoblastic leukemias, upper respiratory tract cancers, head and neck cancers and in various types of cancers. The results observed in human patients were confirmed in tumor bearing rats. SADA variations were also investigated in normal humans. An exemplary curve showing variations of alkaline DNase activity in the serum of an acute non-lymphoblastic leukemia patient during therapeutic monitoring is shown in FIG. 6.

Preferably, the SADA measurements are obtained using the following procedures:

1) Temperature of incubation: 50° C.
2) Time and incubation: 60 minutes.
3) Volume of investigated serum: 100 μl. in 900 μl of tris buffer at pH 8 with substrate 500 μg (DNA sodium salt from calf thymus).
4) The presence of $CaCl_2$ and $MgCl_2$ in the incubator medium.
5) Precipitation procedure in ice bath by: addition of saturated solution of $MgSO_4 \cdot 7H_2O$, vortex, addition of 25 N PCA, vortex, 20 min.; centrifugation at 2000 g.

EXAMPLE X

Determination of Serum Alkaline DNase Activity

Blood is obtained by venipuncture (±5 ml), collected in dry tubes without any anticoagulant, maintained at 4° C. maximum 24 h before serum separation. Frozen serum samples at −20° C. do not lose alkaline DNase activity up to several weeks.

Composition of Solutions:

| Solution A (test) | |
|---|---|
| Tris (-hydroxymethtyl) aminomethane | 12.114 g |
| $CaCl_2 \cdot 2H_2O$ | 0.0367 g |
| $MgCl_2 \cdot 6H_2O$ | 1.0165 g |
| $H_2O$ dist. | ad 500 ml |
| pH adjusted to 8 with concentrated HCl. | |
| Solution B (blank) | |
| Tris (-hydroxymethyl) aminomethane | 12.114 g |
| EDTA | 2.7224 g |
| $H_2O$ dist. | ad 500 ml |
| pH adjusted to 8 with concentrated HCl. | |

Solution C (Substrate)

DNA sodium salt, highly polymerized from calf thymus (Sigma product D 1501) is cut with scissors and dissolved in proportions; DNA 500 μg/dist $H_2O$ 400 μl, by using magnetic stirrer in cold room overnight.

Solution D

Saturated aqueous solution of $MgSO_4 \cdot 7H_2O$

Solution E (Precipitating Agent)

2.25 N PCA

Solutions A, B, C are stored at 4° C. and heated up to room temperature before use. PCA is used at ice temperature.

Test Procedure:

| Incubation medium (test) | |
|---|---|
| Solution A | 500 μl |
| Solution C | 400 μl |
| tested serum | 100 μl |

| Incubation medium (blank) | |
|---|---|
| Solution B | 500 μl |
| Solution C | 400 μl |
| tested serum | 100 μl |

Tested serum is added directly before the incubation which is performed at the temperature 50° C. during 60 minutes. The incubation is stopped by the following procedure: Add to each tube 500 μl of the solution D, vortex, then add 1.5 ml of cold solution E, vortex and place the tubes in ice bath at least for 30 minutes. Tubes are centrifuged at 2000 g for 20 minutes. Supernatant is separated immediately after centrifugation.

The optical density of the supernatants is measured in a quartz cell (1 cm pathway) at 260 nm after zeroing the spectrophotometer on distilled water.

The absorbance of the blank is deduced from the absorbance of the test. The results are expressed in international kilounits per liter of serum.

If the measurement of the absorbance of the supernatant is not realized within a couple of hours, the supernatants must be stored at 4° C. overnight. Assays should be done at room temperature.

If absorbance of a sample is higher than the limit of linearity of the spectrophotometer, repeat the assay with the same volume of diluted serum (in distilled water) and correct the calculations by multiplying the results by the dilution factor.

Valid results depend on an accurately calibrated instrument, timing and temperature control.

Tabulation of Results

Units used are defined as follows:

$$\frac{(\text{Abs test} - \text{Abs blank}) \times \text{total vol (ml)} \times 1}{E\,(8.8\,10^{-3}) \times \text{sample vol (ml)} \times \text{time (min)} \times \text{pathway (cm)}}$$

or (Abs test−Abs blank)×$10^3$×56.8=IU/L

For practical reasons, the following units should be used:

(Abs test−Abs blank)×56.8=kilo IU/L or KIU/L

The preferred embodiments have been described, hereinabove. It will be apparent to those skilled in the art that the above methods may incorporate changes and modifications without departing from the general scope of this invention. It is intended to include all such modifications and alterations in so far as they come within the scope of the appended claims or the equivalents thereof.

Having thus described the invention, it is now claimed:

What is claimed is:

1. A method of inhibiting metastasis of breast cancer cells, colon cancer cells, prostate cancer cells, or liver cancer cells in a host, the method comprising at least one of:
   a) orally administering to said host, in need thereof, a first composition consisting essentially of Vitamin C and Vitamin $K_3$ in an amount synergistically effective to inhibit metastasis of said cancer cells; or,
   b) intravenously administering to said host, in need thereof, a second composition consisting essentially of Vitamin C and Vitamin $K_3$ in an amount synergistically effective to inhibit metastasis of said cancer cells.

2. The method of claim 1 further comprises the step of: intraperitoneally administering to said host, in need thereof, said second composition in an amount synergistically effective to inhibit metastasis of said cancer cells.

3. The method of claim 1 wherein said Vitamin $K_3$ is in a bisulfite form.

4. The method of claim 1 wherein the ratio of Vitamin C to Vitamin $K_3$ in the first composition is about 100 to 1.

5. The method of claim 1 wherein the ratio of Vitamin C to Vitamin $K_3$ in the first and second compositions is in the range of about 50 to 1 to 250 to 1.

6. The method of claim 1 further comprising prior to the oral administration,
preparing said first composition by a method that comprises forming capsules containing a predetermined ratio of Vitamin C and Vitamin $K_3$.

7. The method of claim 6 wherein said Vitamin $K_3$ is in a water-soluble powdered form.

8. The method of claim 6 wherein said capsules consist essentially of Vitamin C and Vitamin $K_3$.

9. The method of claim 1 further comprising prior to said intravenous administration
preparing said second composition by a method that comprises formulating a solution for intravenous delivery that consists essentially of Vitamin C and Vitamin $K_3$.

10. The method of claim 9 wherein said preparing comprises:
separately formulating (i) a Vitamin C solution and (ii) a Vitamin $K_3$ solution; and,
mixing (i) and (ii) to formulate said second composition.

11. The method of claim 10 wherein said Vitamin C solution (i) is prepared so that the Vitamin C concentration is about 16.7 mg/ml sodium ascorbate.

12. The method of claim 10 wherein said Vitamin $K_3$ concentration is about 10 mg/ml Vitamin $K_3$.

13. The method of claim 9 wherein said second composition comprises a mixture of about 16.7 mg Vitamin C and about 0.167 mg Vitamin $K_3$ per ml of normal saline.

14. A method of inhibiting tumor growth in a subject which tumor is a breast tumor, a colon tumor, a prostate tumor, a lymphoma, a bronchogenic carcinoma, a nonlymphoblastic leukemia, an upper respiratory tract tumor, a brain tumor, a neck tumor, a lung tumor, or a liver tumor, the method comprising at least one of:
a) orally administering to the subject, in need thereof, a first composition consisting essentially of Vitamin C and Vitamin $K_3$ in an amount synergistically effective to inhibit said tumor growth; or,
b) intravenously administering to the subject, in need thereof, a second composition of Vitamin C and Vitamin $K_3$ in an amount synergistically effective to inhibit said tumor growth.

15. A method for treating breast cancer, prostate cancer, colon cancer, liver cancer, lung cancer, lymphoma, bronchogenic carcinoma, nonlymphoblastic leukemia, upper respiratory tract cancer, brain cancer, or neck cancer, the method comprising the steps of:
orally administering a first composition consisting essentially of Vitamin C and Vitamin $K_3$ at a ratio of 100 to 1;
intravenously administering a second composition consisting essentially of Vitamin C and Vitamin $K_3$ at a ratio of 100 to 1; and,
orally administering a third composition consisting essentially of Vitamin C and Vitamin $K_3$ at a ratio of 100 to 1.

16. The method of claim 15 further comprising the step of:
intravenously administering a second composition consisting essentially of Vitamin C and Vitamin $K_3$ at a ratio of about 100 to 1.

17. The method of claim 16 further comprising the step of:
orally administering a third composition consisting essentially of Vitamin C and Vitamin $K_3$ at a ratio of about 100 to 1.

18. The method of claim 17, wherein said oral administration step comprises the steps of:
prior to conventional cancer treatment, orally administering the first composition at a first frequency; and,
about one day prior to conventional cancer treatment, orally administering the first composition at a second frequency that is higher than said first frequency.

19. The method of claim 18, further comprising the steps of: on the day of, but prior to, the conventional cancer treatment, orally administering the first composition at said first frequency;
on the day of, but prior to, the conventional cancer treatment, intravenously administering the second composition; and,
administering the conventional cancer treatment.

20. The method of claim 19 further comprising the step of:
on the day following the conventional cancer treatment, orally administering, the third composition.

21. The method of claim 20, wherein the first frequency is once every five hours and the second frequency is once every two hours.

22. The method of claim 21, wherein on the day of, but prior to, the conventional cancer treatment the first composition is orally administered between about 30 minutes and about 180 minutes prior to the conventional cancer treatment; and,
the second composition is intravenously administered between about 30 minutes and about 180 minutes prior to the conventional cancer treatment.

23. The method of claim 22, wherein the cancer is breast cancer or liver cancer.

* * * * *